United States Patent [19]

Manning et al.

[11] Patent Number: 4,915,910
[45] Date of Patent: Apr. 10, 1990

[54] CORROSION MONITORING APPARATUS

[75] Inventors: Michael I. Manning, Dorking; Allan G. Crouch, Horsham; Bernard Lloyd, Fetcham, all of United Kingdom

[73] Assignee: Central Electricity Generating Board, London, United Kingdom

[21] Appl. No.: 30,722

[22] Filed: Mar. 25, 1987

[30] Foreign Application Priority Data

Mar. 26, 1986 [GB] United Kingdom ............... 8607492
Jun. 13, 1986 [GB] United Kingdom ............... 8614400

[51] Int. Cl.$^4$ .................... G01N 7/00; G01N 33/00
[52] U.S. Cl. ................... 422/53; 73/865.6; 436/6
[58] Field of Search .............. 73/865.6; 422/53; 436/6

[56] References Cited

U.S. PATENT DOCUMENTS

| | | | |
|---|---|---|---|
| 4,282,181 | 8/1981 | Pierce | 422/53 |
| 4,338,097 | 7/1982 | Turner et al. | 436/6 |
| 4,539,846 | 9/1985 | Grossman | 422/53 |

FOREIGN PATENT DOCUMENTS 1016737 1/1966 United Kingdom .

OTHER PUBLICATIONS

Champion; Corrosion Testing Procedures; 2nd Edition; John Wiley & Sons; New York, 1965, pp. 97, 132–153, 242.

Primary Examiner—Robert J. Hill, Jr.
Assistant Examiner—Lyle Alfandary-Alexander
Attorney, Agent, or Firm—Willian Brinks Olds Hofer Gilson & Lione

[57] ABSTRACT

The apparatus comprises a stack of corrosible members retained in position by a support, and measurement means, for example a dial gauge, arranged to measure any change in the height of the stack when exposed to a corrosive environment. Electrical potentials and/or mechanical stress can be applied to the stack in order to ascertian the influence thereof on corrosion. The use of a plurality of corrodible surfaces enables amplification of dimensional changes and enables measurements to be obtained in a relatively short time.

18 Claims, 3 Drawing Sheets

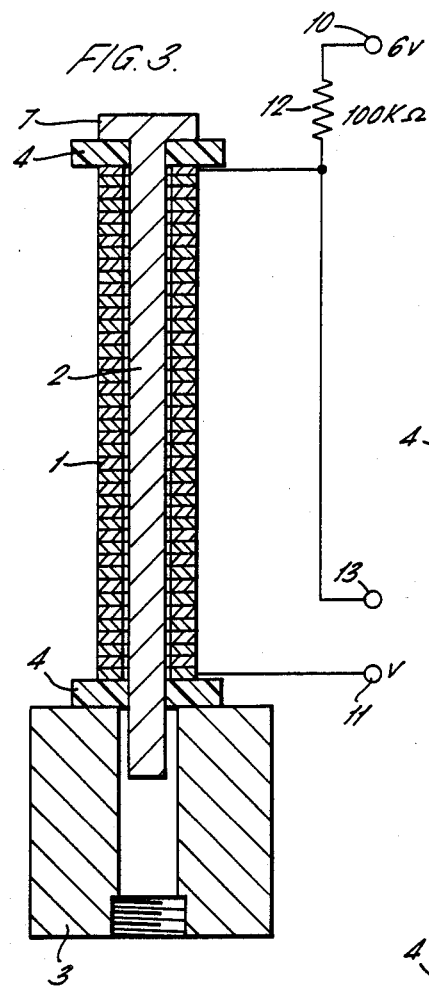
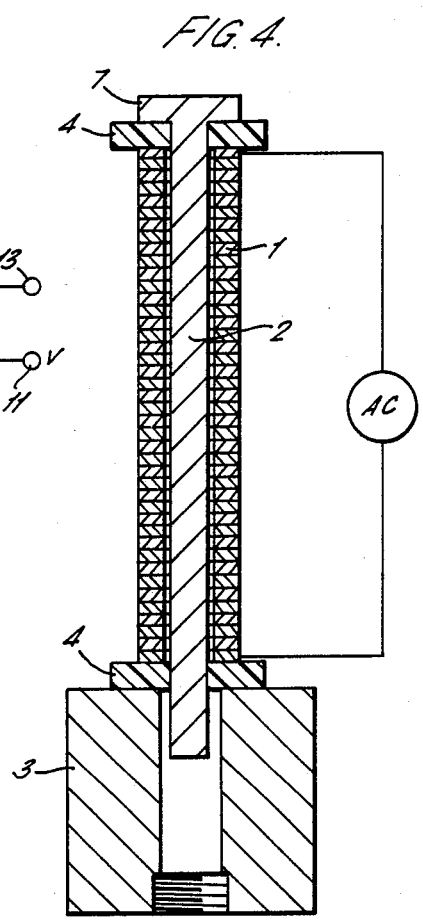

CORROSION MONITORING APPARATUS

FIELD OF THE INVENTION

This invention relates to corrosion monitoring apparatus.

BACKGROUND OF THE INVENTION

Corrosion due to the environment causes problems in many areas, a particular area being the metal reinforcement members often used in buildings. When such members corrode their dimensions increase, this resulting in damage to the building requiring costly repairs.

There is thus a need for corrosion monitoring apparatus which can be used to determine the corrosivity of different environments and to measure displacements caused by corrosion, such information being useful in material selection and in specifying corrosion protection.

A known method of monitoring corrosion is to expose a metal plate to an environment, and then examine the plate in order to ascertain the effect of the environment thereon.

This method suffers from the disadvantages that the exposure period required is generally very long, ie. of the order of years, and that the examination of the plate is time consuming and expensive.

SUMMARY OF THE INVENTION

According to this invention there is provided corrosion monitoring apparatus comprising a plurality of corrosible members arranged each with at least one surface in contact with a surface of another member, and measurement means responsive to changes in a dimension of the arrangement of members.

Preferably the members are arranged in a stack, in which case the members can be apertured, the apparatus including a support passing freely through an aperture in each member and serving to retain the members in the stack. Metal, for example mild steel, washers are particularly suitable for use as the corrosible members.

In the apparatus of this invention a plurality of corrosible surfaces contribute to the displacement sensed by the measurement means, and it has been found that meaningful results can be obtained with the apparatus after only a few days.

The sensitivity of the apparatus can be changed by changing the number of corrosible members used.

DESCRIPTION OF THE DRAWINGS

This invention will now be described by way of example with reference to the drawings, in which:

FIG. 3 is a sectional view of part of an apparatus according to the invention arranged to indicate the time-of-wetness of the corrosible surfaces in the apparatus;

FIG. 4 is a sectional view of part of an apparatus according to the invention arranged to determine the effect of electrical voltages on the corrosion of the corrosible members in the apparatus;

DESCRIPTION OF THE PREFERRED EMBODIMENTS

Figure 1:
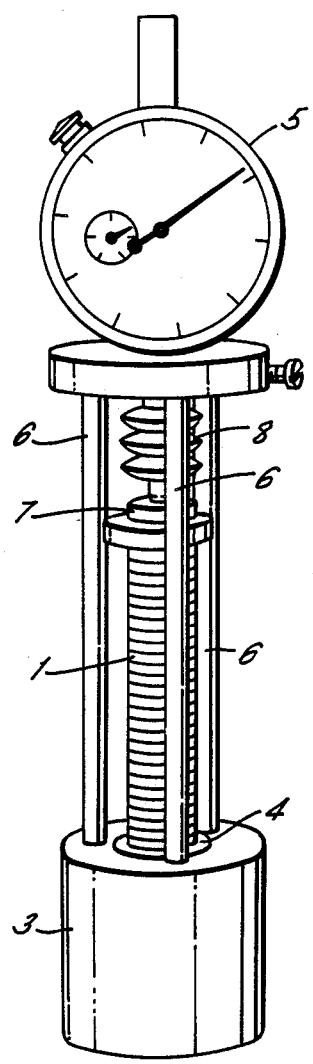
FIG. 1 is a perspective view of apparatus according to the invention.
Figure 2:
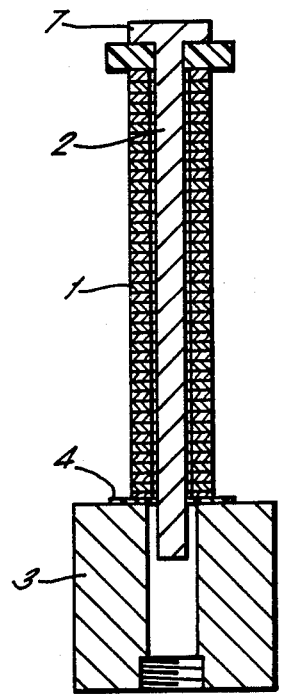
FIG. 2 is a sectional view through part of the apparatus of FIG. 1.

Referring to FIGS. 1 and 2 of the drawings, the apparatus here shown comprises a plurality of corrosible members in the form of mild steel washers 1 arranged in a stack, the stack having a PTFE sheathed metal support 2 passing freely through the aperture in each washer 1 and serving to retain the washers 1 in the stack.

The stack of washers 1 is supported with one end of the stack on a stainless steel base 3, a PTFE disc 4 being interposed between the stack and the base 3.

A measurement means in the form of a dial gauge 5 reading to $+$ or $-1$ micron is mounted in fixed relationship to the base 3 and adjacent the end of the stack of washers 1 remote from the base 3, by means of three mounting members 6 extending between the base 3 and the gauge 5. The mounting members 6 are formed by PTFE sheathed mild steel rods whereby they ar electrically and corrosivley shielded and have a coefficient of thermal expansion matched to that of the stack of washers 1.

As shown, the support 2 terminates at its upper (as seen in the drawing) end in an enlarged head 7, and the gauge 5 has an operating member which engages this head 7. A waterproof seal in the form of a bellows 8 extends between the head 7 and the gauge 5 about the operating member of the gauge 5.

For use, the apparatus described above is placed in a corrosive environment which will cause corrosion of the washers 1, the gauge 5 having been zeroed.

The gauge 5 is thereafter read at suitable intervals according to the expected corrosivity of the environment and the sensitivity of the gauge 5, for example daily near the sea with a gauge readable to two microns, or weekly in an inland rural site with a similar gauge. From the difference between successive readings of the gauge 5 divided by the time interval between the readings and the total number of washer corrosive surfaces, a corrosion rate in, for example, microns per surface per annum, can be calculated.

Although in the apparatus described above the corrosive members are mild steel washers it will be appreciated that members of any other corrosible material or materials of interest can otherwise be used. For example the stack can comprise alternate washers of two different materials, eg iron and zinc, whereby the effect of galvanic action on corrosion can be investigated. By burying at least part of the stack in the earth the corrosive effect of the earth can be determined, this being useful in the design of buried cathodic protection systems for metal and concrete structures.

It will be understood that "corrosion" as used herein is not limited to the eating away or similar degradation of metallic members but can include the eating away or similar degradation of members of other materials. Accordingly, if the stack comprises washers of plastics or rubber material and is immersed in a fluid such as a lubricant or a hydraulic pressure fluid, the corrosive effects of such fluid on the plastics or rubber material can be investigated.

Although the apparatus described above utilises a dial gauge as the measurement means, other devices responsive to displacement in the washer stack, for example an electro-mechanical displacement transducer and in particular a linear voltage displacement transducer, can otherwise be used whereby automatic logging of readings can be carried out.

The apparatus described above can be used either in the open at sites where the corrosivity of the atmosphere is being measured, or otherwise in, for example, environmental cabinets to measure the corrosivity of particular controlled atmospheres.

Apparatus according to the invention can be used to measure corrosion in many circumstances other than simple exposure to a corrosive environment, and a number of such uses will now be described with reference to FIGS. 3 to 6 of the drawings.

Each apparatus to be described is basically the same as that described with reference to FIGS. 1 and 2, and the same reference numerals have been used for corresponding parts. The measuring means (dial gauge) shown in FIG. 1 has been omitted in each case for reasons of clarity. It will be appreciated that each apparatus to be described when complete includes such a measuring means which serves to indicate any changes in the height of the stack of members resulting from corrosion of the corrosible members.

In the apparatus of FIG. 3 the stack comprises a plurality of mild steel washers 1 having at each end an electrically insulating PTFE guide disc 4. An electrical voltage is applied across the stack of washers 1, the top and bottom washers 1 being connected to input terminals 10 and 11, the top washer 1 by way of a resistor 12, while a resistance measuring device (not shown) is connected between terminal 11 and a further terminal 13 which is directly connected to the top washer 1 in the stack.

This apparatus serves to determine the time-of-wetness, that is the time for which each corrosible surface in the stack is wet, this being an important variable in corrosion studies. After some corrosion the resistance of the stack will be high during dry conditions and low during wet conditions. Thus, the device connected to terminals 11 and 13 will indicate the time-of-wetness, and this value can be included in the corrosion rate calculations carried out.

The apparatus shown in FIG. 4 is similar to that shown in FIG. 3, but simply has a source of AC (or DC) connected between the top and bottom washers 1 in the stack. By logging the voltages applied to the stack the effect of such voltages on corrosion can be determined.

Figure 5:
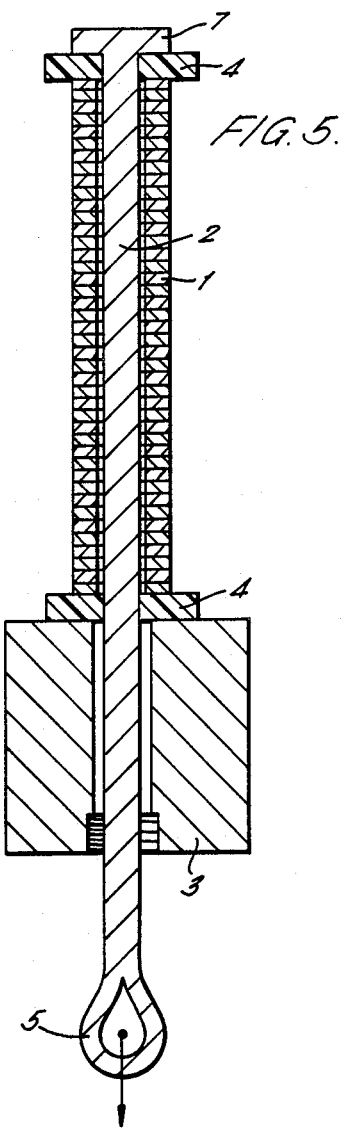
FIG. 5 is a sectional view of part of an apparatus according to the invention arranged to determine the effect of stress on the corrosion of the corrosible members of the apparatus.

In the apparatus shown in FIG. 5, the support 2 extends throught the base 3 and terminates in an eye 5 on which weights can be hung. This apparatus can be used to investigate the effect of the stress imposed by applied weights on the corrosion of the washers 1 as measured by the measuring means (not shown).

Figure 6:
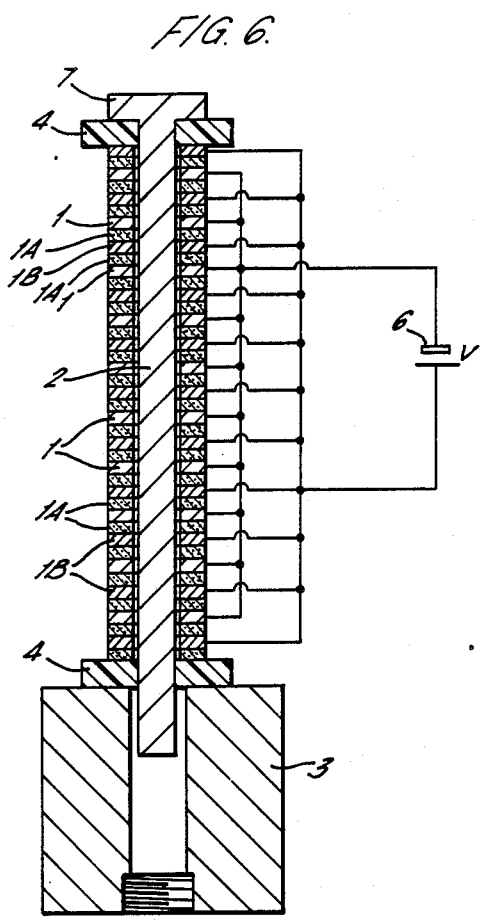
FIG. 6 is a sectional view of part of an apparatus according to the invention arranged to determine corrosion between surffaces of dissimilar materials.

The apparatus shown in FIG. 6 can be used to determine the corrosion rate of steel in concrete, whereby the processes influencing concrete reinforcement corrosion can be studied, and also control of such corrosion by cathodic protection. In this apparatus the stack comprises corrosible mild steel washers 1 each sandwiched between a pair of concrete washers 1A, with adjacent concrete washers 1A being separated by non-corrosible electrically conductive washers 1B. The corrosible washers 1 are connected to one terminal, and the non-corrosible conductive washers 1B are connected to the other terminal, of a voltage source 6.

An electrical supply as described with reference to FIGS. 3 and 4 and/or a stress arrangement as described with reference to FIG. 5, can be used with the apparatus of FIG. 6.

We claim:

1. Corrosion monitoring apparatus coprising:
   a plurality of corrosible members each having an aperture formed therein and being arranged in a stack each with at least one surface in contact with a surface of another member;
   a support passing freely through an aperture in each member and serving to retain the members in the stack; and
   measurement means responsive to an increase in a dimension of the arrangement of members.

2. Apparatus as claimed in claim 1, in which the support is of plastics-coated metal.

3. Apparatus as claimed in claim 1, in which the measurement means comprises a dial gauge.

4. Apparatus as claimed in claim 1, in which the measurement means comprises an electro-mechanical displacement tansducer.

5. Apparatus as claimed in claim 1, in which the members are metal washers.

6. Apparatus as claimed in claim 1, in which the members are of plastics material.

7. Apparatus as claimed in claim 1, in which the members are of rubber.

8. Apparatus as claimed in claim 1, including means to apply an electrical potential across the stack of members.

9. Apparatus as claimed in claim 8, including an electrical resistance measuring device connected across the stack of members.

10. Apparatus as claimed in claim 1, including means to mechanically stress the members.

11. Apparatus as claimed in claim 10, in which the support extends downwards through the stack of the members and has means for applying weight thereto to produce said stress.

12. Apparatus as claimed in claim 1, in which the stack comprises a plurality of corrosible metal members each sandwiched betwen a pair of concrete members, with adjacent concrete members being separated by a member of non-corrosible metal.

13. Apparatus as claimed in claim 12, in which the corrosible members are connected to one terminal of an electrical potential source and the non-corrosible metal members are connected to the other terminal of the electrical potential source.

14. Apparatus as claimed in claim 1, in which the stack of members is supported with one end of the stack on a base, the measurement means being mounted in fixed relationship to the base.

15. Apparatus as claimed in claim 14, in which the measurement means is mounted adjacent the end of the stack of members remote from the base, by means of one or more mounting members extending between the base and the measurement means.

16. Apparatus as claimed in claim 15, in which each mounting member is electrically and corrosively shielded and has a coefficient of thermal expansion matched to that of the stack of members.

17. Apparatus as claimed in claim 16, in which each mounting member is of plastics-coated metal.

18. Corrosion monitoring apparatus comprising:

means for contiguously arranging in a stack along an axis a plurality of members, at least two of which are corrosible;

support means passing freely through an aperture in each member to retain the members in the stack; and means for measuring along said axis dimensional increases of the composite of the members.

* * * * *